United States Patent
Inamdar

(10) Patent No.: US 10,804,769 B2
(45) Date of Patent: Oct. 13, 2020

(54) SURGICAL INSTRUMENT WITH PHASE CHANGE COOLING

(71) Applicant: COVIDIEN LP, Mansfield, MA (US)

(72) Inventor: Tejas Satish Inamdar, Boston, MA (US)

(73) Assignee: Covidien LP, Mansfield, MA (US)

( * ) Notice: Subject to any disclaimer, the term of this patent is extended or adjusted under 35 U.S.C. 154(b) by 301 days.

(21) Appl. No.: 15/579,842

(22) PCT Filed: Jun. 15, 2016

(86) PCT No.: PCT/US2016/037611
§ 371 (c)(1),
(2) Date: Dec. 5, 2017

(87) PCT Pub. No.: WO2016/205359
PCT Pub. Date: Dec. 22, 2016

(65) Prior Publication Data
US 2018/0375402 A1   Dec. 27, 2018

Related U.S. Application Data

(60) Provisional application No. 62/180,995, filed on Jun. 17, 2015.

(51) Int. Cl.
*H02K 9/19* (2006.01)
*A61B 17/32* (2006.01)
(Continued)

(52) U.S. Cl.
CPC ........... *H02K 9/19* (2013.01); *A61B 17/1622* (2013.01); *A61B 17/1644* (2013.01);
(Continued)

(58) Field of Classification Search
CPC ................... B23B 45/044; H01L 35/30; A61B 2017/00084; A61B 2017/00398;
(Continued)

(56) References Cited

U.S. PATENT DOCUMENTS 1,585,934 A   5/1926  Muir
1,666,332 A   4/1928  Hirsch
(Continued)

FOREIGN PATENT DOCUMENTS

DE   3206381 A1   9/1983
DE   3339322 A1   5/1984
(Continued)

*Primary Examiner* — Shaun L David
*Assistant Examiner* — Mohamed G Gabr
(74) *Attorney, Agent, or Firm* — Carter, DeLuca & Farrell LLP

(57) ABSTRACT

Systems and methods are discussed herein for cooling a surgical handset using a phase-change material. A container filled with a phase-change material may be telescoped over a heat-generating mechanism of a surgical handset, such as a battery and/or a motor. When the surgical handset is activated, the heat generated by the heat-generating mechanism is absorbed by the phase-change material in the container, which transitions from a first phase to a second phase.

11 Claims, 6 Drawing Sheets

(51) Int. Cl.
  *H02K 9/22* (2006.01)
  *A61B 17/16* (2006.01)
  *A61B 17/00* (2006.01)
  *H02K 9/20* (2006.01)
  *A61B 18/00* (2006.01)

(52) U.S. Cl.
  CPC ......... *A61B 17/32002* (2013.01); *H02K 9/22* (2013.01); *A61B 2017/00084* (2013.01); *A61B 2017/00398* (2013.01); *A61B 2017/00734* (2013.01); *A61B 2017/1651* (2013.01); *A61B 2018/00005* (2013.01); *H02K 9/20* (2013.01)

(58) Field of Classification Search
  CPC .. A61B 2017/00734; A61B 2017/1651; A61B 2018/00005; A61B 2018/00577; A61B 2018/00023; A61B 17/32002; A61B 17/1644; A61B 17/320758; A61B 17/00; A61B 17/1628; A61B 18/1402; H02K 9/20; H02K 9/22; H02K 9/19; H01K 5/20; H01M 10/613; H01M 10/4235; H01M 10/486; H01M 10/623; H01M 10/63; H01M 10/635; H01M 10/653; H01M 10/6551; H01M 10/6552; H01M 10/6569; H01M 10/659; H01M 2/1094; H01M 2220/30
  See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,073,160 A | 2/1978 | Perret |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,689 A | 10/1995 | Kresch et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |

(56) References Cited

U.S. PATENT DOCUMENTS

| | | | |
|---|---|---|---|
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,837,847 B2 | 1/2005 | Ewers et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 8,076,022 B1* | 12/2011 | Tsukamoto ....... H01M 10/4235 |
| | | | 429/120 |
| 9,060,801 B1 | 6/2015 | Cesarini et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165549 A1* | 11/2002 | Owusu-Akyaw ............... |
| | | | A61B 17/1628 |
| | | | 606/80 |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1 | 3/2006 | Shener et al. |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2015/0327905 A1 | 11/2015 | Barth et al. |
| 2016/0285345 A1* | 9/2016 | Adimula ................. H02K 5/18 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1623677 A1 | 2/2006 |
| EP | 1681022 A1 | 7/2006 |
| EP | 1820987 A2 | 8/2007 |
| GB | 2093353 A | 9/1982 |
| GB | 2311468 A | 10/1997 |
| JP | H0175416 U | 5/1989 |
| JP | 2002529185 A | 9/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |

(56) References Cited

FOREIGN PATENT DOCUMENTS

| | | |
|---|---|---|
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0315831 A1 | 5/2001 |
| WO | 0158368 A1 | 8/2001 |
| WO | 200195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 20070014548 A2 | 2/2007 |
| WO | 2007044833 A2 | 4/2007 |
| WO | 2012044705 A1 | 4/2012 |

* cited by examiner

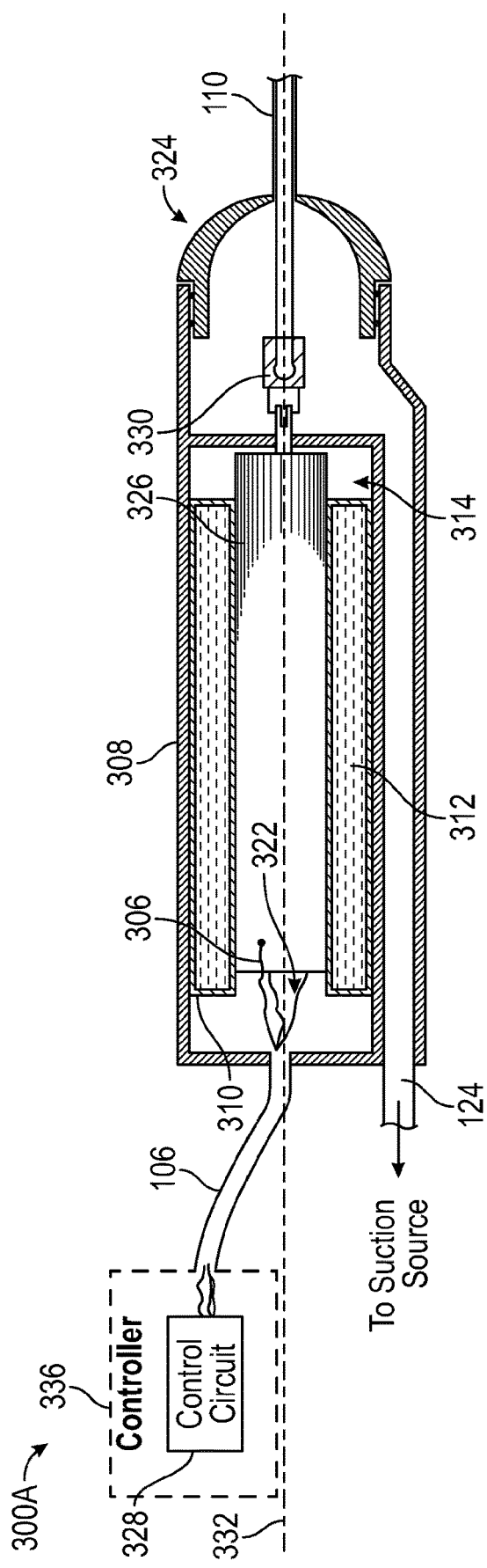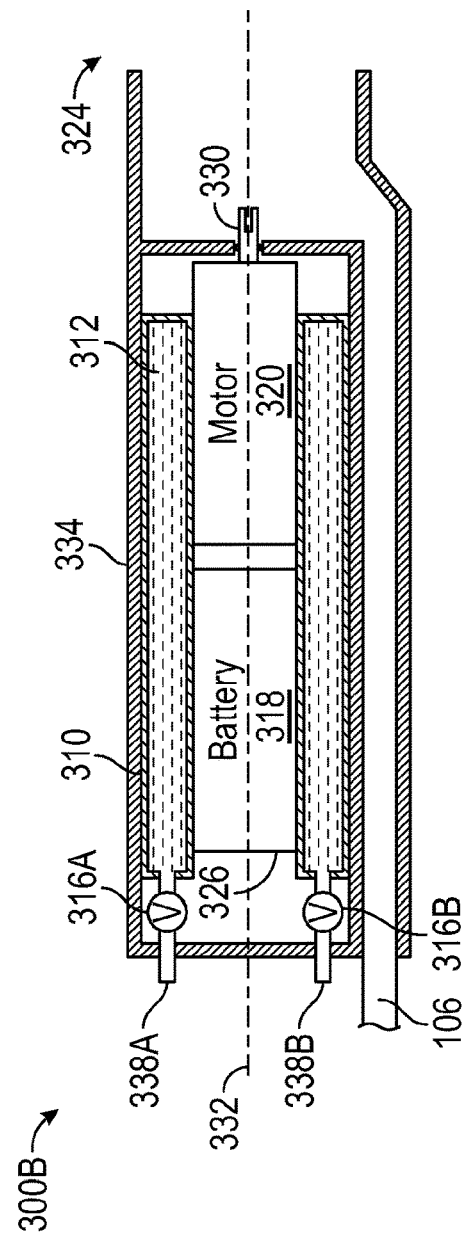

US 10,804,769 B2

SURGICAL INSTRUMENT WITH PHASE CHANGE COOLING

CROSS-REFERENCE TO RELATED APPLICATIONS

This application claims the benefit of U.S. Provisional Application No. 62/180,995 titled "Surgical Instrument with Phase Change Cooling," filed Jun. 17, 2015. The provisional application is incorporated by reference herein as if reproduced in full below.

BACKGROUND

Many handheld surgical devices utilize electric motors for power. The electric motor of a handheld device generates heat and must be cooled to ensure effective and comfortable operation, since overheating of an electric motor can result in permanent damage to the motor and render a surgical device inoperable. Electric motors are also subject to safety requirements, such as the IEC 60601-1-2:1993, which limit the maximum allowable surface temperature of a handheld device.

SUMMARY

In an embodiment, a tissue removal system, comprising: a motor drive unit (MDU) that comprises a proximal end, a distal end, a motor and a drive shaft, an overall length, and a heat-generating mechanism disposed at least partially within the MDU; a mechanical resection device comprising a shaft, a resection tip at the distal end of the shaft, and a connector assembly on a proximal end of the shaft, the mechanical resection device removably coupled to the distal end of the MDU and rotationally coupled to the drive shaft by way of the connector assembly; and a first container that defines a first closed volume, the first container thermally coupled to the heat-generating mechanism; and a first phase-change material disposed within the first closed volume, the first phase change material thermally coupled to the heat-generating mechanism by way the first container.

In an embodiment, a method of using a motor drive unit, comprising: coupling a mechanical resection device to a distal end of a handset comprising a heat-generating mechanism and a container that defines a closed volume, the container thermally coupled to the heat-generating mechanism; and activating the mechanical resection device, wherein the heat-generating mechanism generates heat in response to activation; absorbing, by a phase-change material disposed within the first closed volume and associated with a phase change temperature, at least some of the heat generated and thereby causing the phase-change material to change phase from a first phase to a second phase, wherein the phase-change material is thermally coupled to the heat-generating mechanism by way of the container; in response to a determination that the temperature of the phase-change material is greater than the phase change temperature, automatically deactivating the instrument.

In an embodiment, a method of cooling a heat-generating unit, comprising: activating an instrument coupled to a heat-generating mechanism, the heat-generating mechanism comprising a distal end, a proximal end, a central axis, a temperature sensor, an overall length, a control circuit associated with the MDU and electrically coupled to the temperature sensor; and a container that defines a closed volume, the container thermally coupled to the heat-generating mechanism; and generating heat, by the heat-generating unit, in response to the activation; absorbing, by a phase-change material disposed within the first closed volume, the phase change material associated with a phase change temperature and thermally coupled to the heat-generating mechanism by way of the container, at least some of the heat generated and thereby causing the phase-change material to change phase from a first phase to a second phase; reading, by the control circuit, a temperature of the phase-change material; and automatically deactivating, by the control circuit, the motor when the value indicative of temperature of the phase-change material the phase change temperature.

BRIEF DESCRIPTION OF THE DRAWINGS

For a detailed description of exemplary embodiments of the invention, reference will now be made to the accompanying drawings in which:

FIG. 3A shows a cross-section of a handset according to certain embodiments of the present disclosure.

FIG. 3B shows a partial cross-section of a handset according to certain embodiments of the present disclosure.

DEFINITIONS

Figure 1:
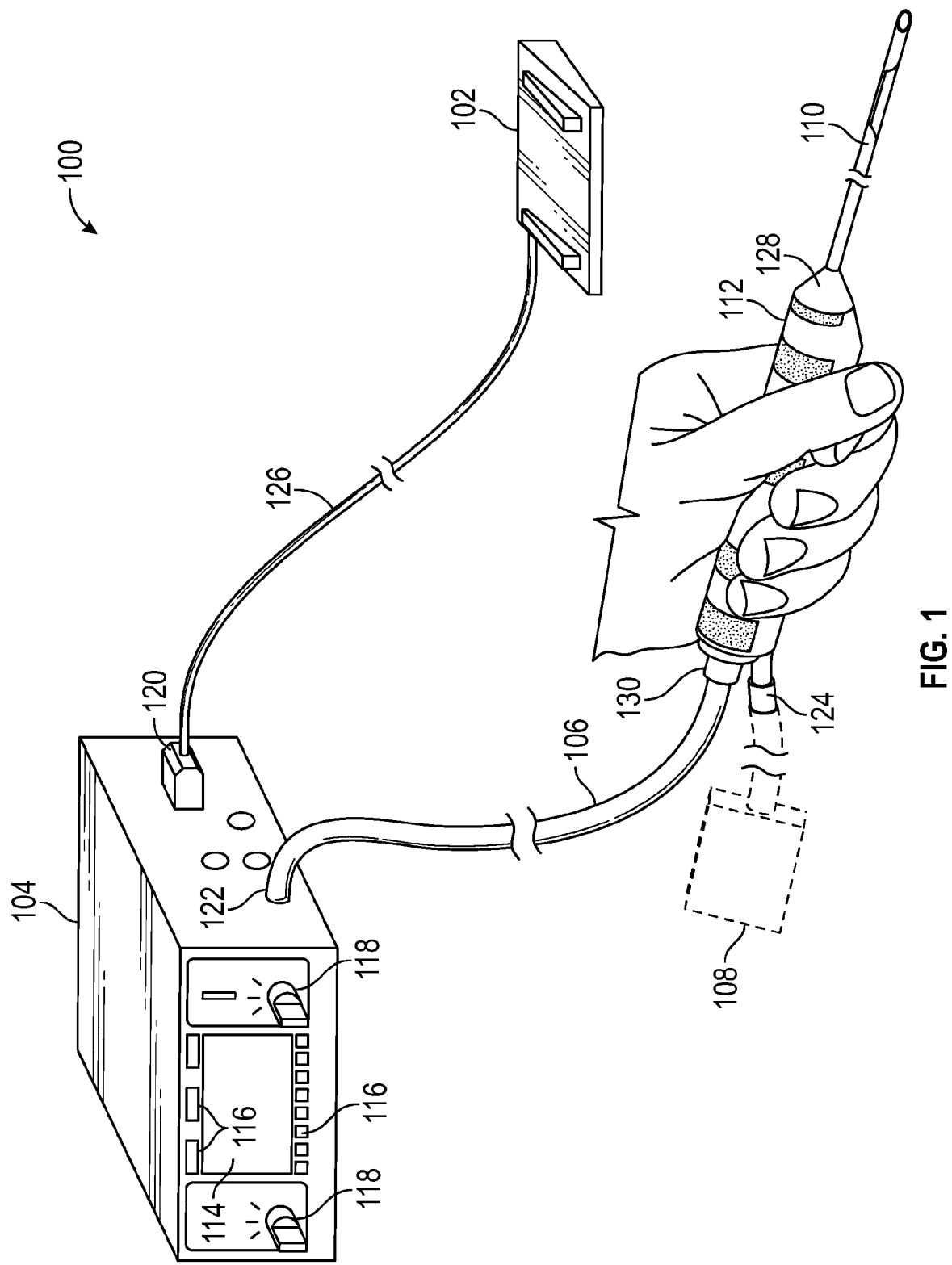
FIG. 1 shows a surgical system according to certain embodiments of the present disclosure.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Heat-generating mechanism" shall mean a component of an electromechanical surgical device (such as, but not limited to, a battery or a motor) that generates heat upon activation and during use in a surgical procedure.

"Heat-absorbing mechanism" shall mean a component comprising a sealed volume that contains a phase-change material and configured to absorb at least some heat generated by a heat-generating mechanism.

"Phase-change material" shall mean a liquid, gas, solid, colloidal, or other material such as inorganic salts, organic materials, or combinations thereof which exist as different phases at different temperatures and transition between different phases in response to a change in temperature. Atmospheric air shall not be considered a phase-change material.

"Mechanical resection device" shall mean an instrument for use in a surgical procedure to remove tissue and/or resect tissue, including shavers, burrs, morcellators, and other surgical instruments.

"Removably coupled" shall mean a first component coupled to a second component such that first component can be decoupled from the second component without destroying or rendering the first or second components non-functional.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Surgeons use handheld surgical devices to perform surgical procedures on a patient. Many handheld surgical devices are powered by an electric motor, battery, or other heat-generating mechanism, which generates heat and must be cooled to ensure the effective and comfortable operation of the handheld surgical devices. Overheating of an electric motor or battery can permanently damage the motor or the battery and render a surgical device inoperable. Electric motors are also subject to safety requirements, such as the IEC 60601-1-2:1993, which limit the allowable surface temperature of a handheld device.

Many handheld surgical devices use flowing fluid, saline or water, to cool the heat-generating mechanism such as an electric motor, which may alternatively be referred to as a "heat-generating unit." However, this fluid cooling method may be problematic for a number of reasons. First, in order to cool the electric motor sufficiently, a high rate of fluid flow may be employed but may not be possible due to the nature of the surgery or the design of the surgical device. Second, the small size and design of a surgical device may not permit room for a fluid channel close enough to the electric motor to provide sufficient cooling. Third, the lumen of the fluid channel may get clogged and slow the flow rate, resulting in overheating of the electric motor. Other handheld surgical devices may use air flow to cool the electric motor. This cooling method is also problematic because the small size and design of a surgical device may not permit room for a device to generate air flow, or provide sufficient room to permit the air flow to adequately cool the electric motor.

Using the systems and methods discussed herein, a handset may be cooled during operation using a container filled with a phase-change material (PCM). The phase-change material cools the electric motor by extracting heat from the electric motor using the latent heat of fusion of the phase-change material. The phase-change material extracts heat and changes from a first phase to a second phase in response to absorbing the heat, until a phase transition temperature is reached. For example, if the phase transition temperature for the phase-change material is 36° C., and the latent heat of fusion is 230 kJ/kg, then 10 g of the phase-change material at 36° C. can absorb 2.30 kJ of heat and maintain a constant temperature of 36° C. The phase-change material maintains this temperature while it changes phase from solid to liquid. The phase-change material absorbs heat to keep the temperature of the electric motor constant, and the electric motor or battery may be automatically deactivated in response to a determination that the phase-change material has transitioned from a first phase to a second phase.

In an embodiment, a single container may be telescoped over a heat-generating mechanism of a handset, this single container may be sealed, refillable, disposable, or reusable. In alternate embodiments, a plurality of containers may be telescoped over the heat-generating mechanism and over each other, some or all of said containers may be disposable and some or all may be reusable. A reusable container may be one where the second phase transitions back to the first phase after use (e.g., the container cools down and reverts to the first phase), or a container configured to have the phase-change material removed and refilled. In some embodiments, the container may be telescoped over the heat-generating mechanism in an assembled handset, and in alternate embodiments the container or containers may be telescoped and/or filled by a surgeon or surgical support team member prior to an operation.

FIG. 1 shows a surgical system 100 that may be used for various surgical procedures including tissue resection and removal. In an embodiment, the system 100 comprises a control unit 104 coupled to a handset 112 via a line 106. The control unit 104 may be coupled to a proximal end 130 of the handset 112 via the line 106 to supply power to the handset 112, such power may be regulated by the use of a foot switch 102. The control unit 104 may comprise a digital interface 114 that may be a graphical user interface and, in some embodiments, the digital interface 114 be a touch screen. In some embodiments, the control unit 104 may be coupled to a wall outlet or may comprise a rechargeable battery and may comprise a plurality of buttons 116 and control knobs 118 that may aid in the use and control of the operation of the handset 112. The system 100 further comprises a power port 120 of the control unit 104 that may be coupled to a foot switch 102 via a line 126. The handset 112 may be coupled to an instrument 110 at the distal end 128 of the handset 112, the instrument 110 may comprise a burr, blade, or other instrument 110. The handset 112 may also comprise at least one circuit board (not shown) and a plurality of motion, force, and temperature sensors (not shown). In an embodiment, measurements taken by the sensors may be displayed using the digital interface 114.

In an embodiment, the handset 112, including the rotational, axial, and other motion of the instrument 110, may be controlled by a motor within the handset 112 (motor not shown) activated by the foot switch 102. The motor may generate heat upon activation and for the duration of use of the handset 112. In an embodiment, there may also be a suction source 108 coupled to the handset 112 via a fluid line 124 that extends from the proximal end 130 of the handset towards the distal end 128, and is shown in more detail below. The suction source 108 may be coupled to a fluid source or may contain a fluid source, and the fluid line 124 may be employed during a surgical procedure.

The phase-change material discussed herein is not shown in FIG. 1 but may be in a container telescoped over a heat-generating mechanism of the handset 112 such as the motor so that the user of the handset benefits from the cooling/heat-removal properties of the phase-change material without interrupting the use of the handset 112. As discussed in detail below, the container in which the phase-change material is disposed may be thermally, mechanically, and electrically coupled to one or more sensors in order to enable an automatic shutoff feature. In some embodiments, there may be an additional fluid line outside of the container but within the handset which may be used to circulate fluid during the procedure to provide additional cooling to the heat-generating mechanism.

Figure 2:
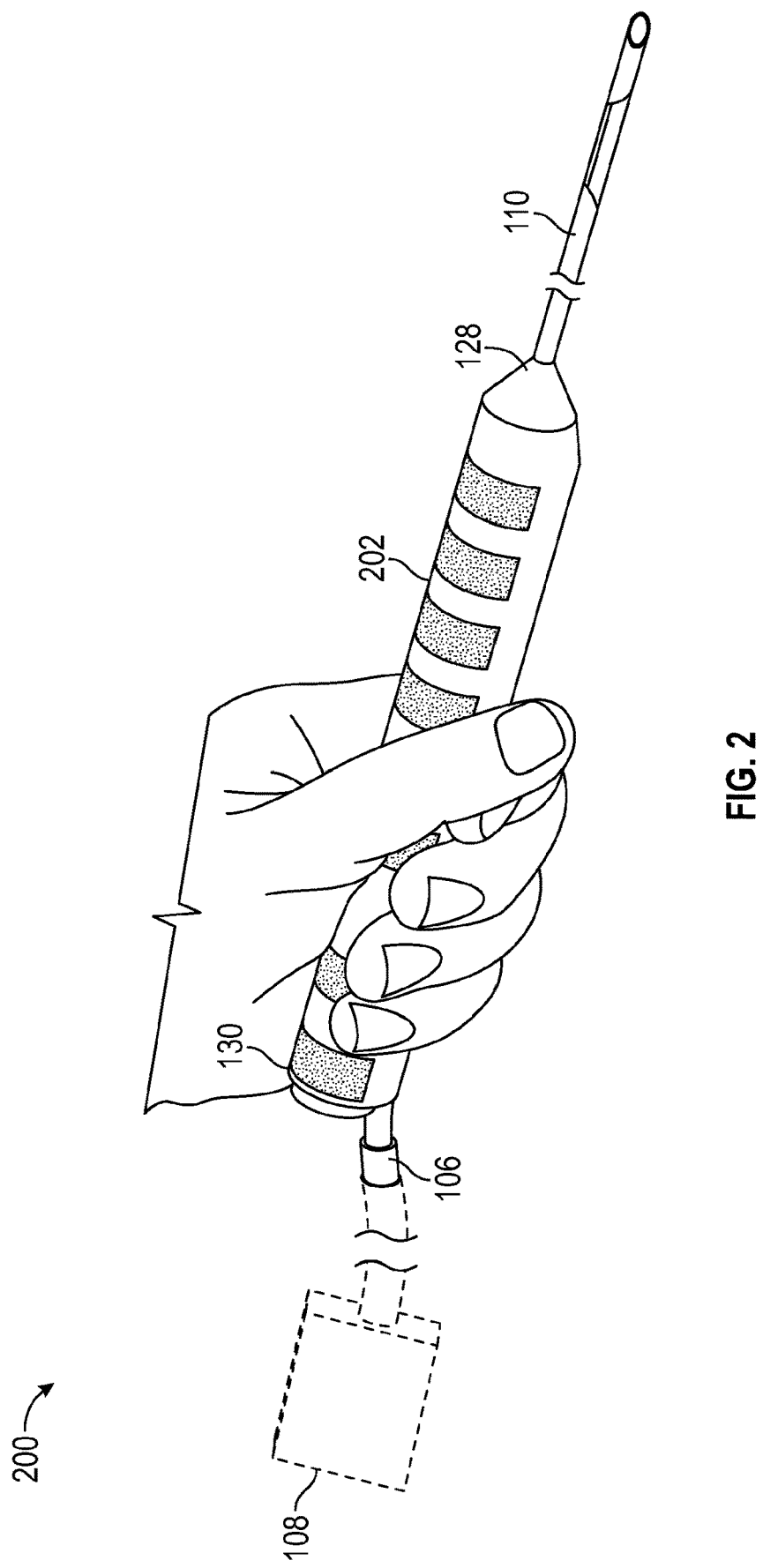
FIG. 2 shows a surgical system according to certain embodiments of the present disclosure.

FIG. 2 is an illustration of an alternate embodiment of a surgical system 200 comprising a handset 202 coupled to an instrument 110 at a distal end 128 of the handset 202. In accordance with some embodiments, a phase-change material may be used to cool handheld devices such as the handset 202 that make use of batteries in order to make the device portable and/or wireless. In such situations, charging or discharging of battery power may result in heat generation during the operation of the device, and the heat-generating mechanism, e.g., the battery and/or the motor, may have a container filled with phase-change material telescoped over the container. FIG. 2 also illustrates that the handset 202 is coupled to a suction source 108 at the proximal end 130 via a fluid line 124. In contrast to the handset 112 in FIG. 1, the handset 202 contains both a motor and a battery (not shown) and may not employ a control unit, thus creating a less-wired option for surgery. Therefore, the handset 202 in FIG. 2 can be operated in the absence of a power connection line and a control unit when the battery is sufficiently charged. In an embodiment, the handset 202 is activated and the battery supplies power to the device, including the motor, and heats up, a container of phase-change material telescoped over the battery absorbs the heat generated by the battery. In some embodiments, the container of phase-change material may be telescoped over the battery and at least part of the motor adjacent to the battery, and the phase-change material absorbs heat generated during operation by both the battery and the motor.

FIG. 3A an embodiment 300A of a handset 308 comprising a phase-change material 312. FIG. 3A illustrates the handset 308 and a container 310 comprising the phase-change material 312, the heat-generating mechanism 314 is telescoped into the container 310 along a central axis 332. In an embodiment, the heat-generating mechanism may comprise a motor 314, and the container 310 may be coupled to a stator 326 of the motor 314. The handset 308 may be coupled to a controller 336 that comprises a control circuit 328. The handset may comprise a plurality of sensors 306 that may include a temperature sensor, motion sensor, force sensor, and other sensors. The instrument 110 may be coupled to the handset 308 via the coupler 330, and the plurality of sensors may be coupled to the controller 336 vial the line 106.

Prior to absorbing heat, the phase-change material 312 is in a first state (e.g., liquid or solid) and is associated with a phase-change temperature such that, as the handset 308 is activated and the motor 314 generates heat, the phase-change material 312 absorbs at least some of the heat generated and transforms from the first phase to a second, different phase. In an embodiment, the phase-change material 312 may be solid at room temperature and may be configured to transition to a liquid as heat is absorbed. In alternate embodiments, the phase-change material 312 is a liquid at room temperature and is configured to transition to a gas as heat is absorbed. The temperature sensor 306 is thermally coupled to the container 310, and the control circuit 328 is electrically coupled to the temperature sensor 306. The temperature sensor 306 is thereby configured to read the temperature of the phase-change material 312 in the container 310 during the use of the handset 308.

In an embodiment, the control circuit 328 is configured to read, from the temperature sensor 306, a value indicative of temperature of the phase-change material 312 during the operation of the handset 308. The control circuit 328 is further configured to deactivate the motor 314 of the handset 308 when the value indicative of temperature exceeds a predetermined threshold. The predetermined threshold, which may be referred to as a trigger, may comprise a temperature above the phase change temperature of the phase-change material 312, e.g., a temperature indicating the phase-change material 312 has fully transitioned from a first phase to a second phase (e.g., a temperature above the phase change temperature).

FIG. 3B shows a side elevation, partial cross-sectional, view of an embodiment 300B. FIG. 3B illustrates the handset 334 and a container 310 comprising the phase-change material 312, which may be similar to that described in FIG. 3A. In the embodiment 300B, the container 310 is telescoped over the motor 314 along the shared central axis 332. The container 310 may be thermally and electrically coupled to a battery 318 that may be a rechargeable battery 318 disposed next to a motor 320. The battery 318, the motor 320, or both may be considered the heat-generating mechanism in the embodiment 300B. The handset 334 may comprise the container 310, a control circuit, and a plurality of sensors (not shown). Similarly to FIG. 3A, the plurality of sensors are in communication with the control circuit and may include a temperature sensor, motion sensor, force sensor, and other sensors, and the container 310 may be thermally and/or electrically coupled to at least one sensor such as a temperature sensor. In an embodiment, the handset 334 is activated and the battery 318 supplies power to the motor 320. The battery 318 and the motor 320 may heat up when the battery 318 is powered on to supply power to the motor 320, and the container 310 of phase-change material 312 is telescoped over the battery 318 absorbs the heat generated by the battery 318 as well as the motor 320.

In some embodiments, the container 310 may be single use, and may be removed from the handset 308 and disposed of. In alternate embodiments, the container 310 may be fillable, in that it may be shipped empty and filled prior to use, or refillable, in that it may be shipped empty or full and may have the phase-change material removed and filled/refilled. FIG. 3B further illustrates a first fluid port 338A in fluid communication with a first fluid valve 316A and a second fluid port 338B in fluid communication with a second fluid valve 316B to enable fluid communication with the container 310. In some embodiments, the valves 316A and 316B and/or fluid ports 338A and 338B may be integral to the container. In alternate embodiments, more or less fluid valves and ports may be employed.

In an embodiment, the first valve 316A may be used to introduce the phase-change material 312 from the container 310 prior to a first-time use or after phase-change material has been removed. The second valve 316B may be used to remove the phase-change material 312 from the container 310. In alternate embodiments, the first valve 316A may be used to remove the phase-change material 312 from the container 310, and the second valve 316B may be used to introduce the phase-change material 312 to the container 310. In still other embodiments, for example, if the container 310A is semi-rigid, semi-flexible, or flexible, e.g., it loses at least part of its filled volume when the fluid is removed, both the first and second valves 316A and 316B may both be used to remove and/or introduce fluid to the container 310. In yet still other cases, one valve may be used to fill or drain the container, while the second valve acts as a vent. This container 310 may be referred to as a "refillable" container, since the phase-change material may be introduced and/or introduced, removed, and re-introduced, via the valves 316A and 316B.

Figure 4:
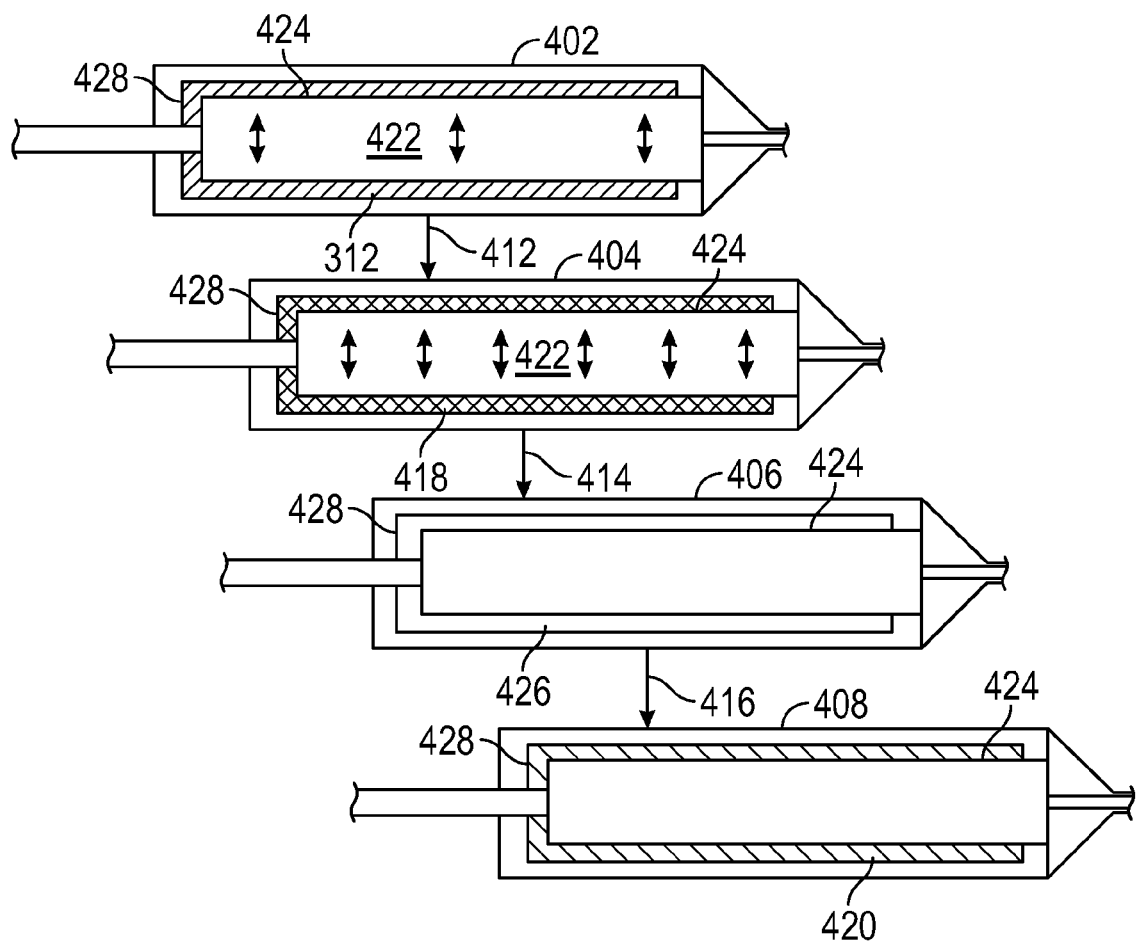
FIG. 4 shows a plurality of partial cross-sectional views of handset used during a surgical procedure according to certain embodiments of the present disclosure.

FIG. 4 shows a plurality of views of handset configurations as the handset is used during surgery, and as the container containing the phase-change material absorbs heat from the heat-generating mechanism and changes from a first phase to a second phase. It is appreciated that FIG. 4 illustrates the handset if shorthand form to show the container 428 and the phase-change materials, and so as not to unduly complicate the figure the illustrations do not include features such as suction, instrumentation, external power, or other features illustrated in other figures herein that may be part of the surgical system. It is also appreciated that the heat generating mechanism 424 in FIG. 4 may represent a motor, a battery, or combinations thereof.

In an embodiment, a first handset configuration 402 comprises a heat-generating mechanism 424 and a container 428 telescoped over the heat-generating mechanism 424 prior to use. The container 428 is filled prior to activation of the handset 402 with a phase-change material 312 that is associated with a first phase 312a and a phase-change temperature. As heat is generated by activation of the handset 402, as indicated by the arrows 422, the phase-change material 312 undergoes a transition indicated by arrow 412 to the second handset configuration 404 where the phase-change material 312 is fully converted to a second phase 418. As discussed above, the phase-change material 312 may comprise a liquid or a solid at room temperature, and the phase-change material 312 after the transition indicated by the arrow 412 may comprise a second phase 418 of a gas or a liquid at the elevated temperature created by the heat generation 422. In an embodiment, a temperature sensor (not pictured) that is a part of the handset in each of the configurations in FIG. 4 is coupled to the container 428 and is used to determine when the phase-change material 312 has reached a predetermined threshold above the phase-change temperature (e.g., when the phase-change material 312 has fully transitioned to the second phase 418), and the heat-generating mechanism 424 is automatically deactivated to allow for disassembly as indicated by arrow 414.

In the third handset configuration 406 as indicated by the arrow 414 in FIG. 4, the container 428 is shown after the phase-change material 312 is removed, leaving an empty 426 container 428. The container 428 may be a rigid container that maintains its shape when empty, as shown in the third configuration 406. In alternate embodiments, the container 428 may be semi-rigid or made of flexible material that expands the container 428 to its shape when the container 428 is filled. It is appreciated that the removal of the phase-change material 312 is performed subsequent to the deactivation of the handset. The phase-change material 312 may be removed by fluid ports comprising valves (not shown), or other ports as appropriate for the container 428 design. The container 428 is shown in FIG. 4 as wrapping around a portion of the proximal end of the handset configurations 402-408, but may in some embodiments terminate prior to the proximal end or not wrap around the proximal end of the heat-generating mechanism. As indicated by the arrow 416, the fourth handset configuration 408 is illustrated and comprises a new phase change material 420 associated with a phase 422, which may comprise a liquid or a solid at room temperature. The phase change material 420 may be introduced to the container 428 through the same port or ports as the material 312 was removed from, or through a dedicated fluid inflow port.

Figure 5:
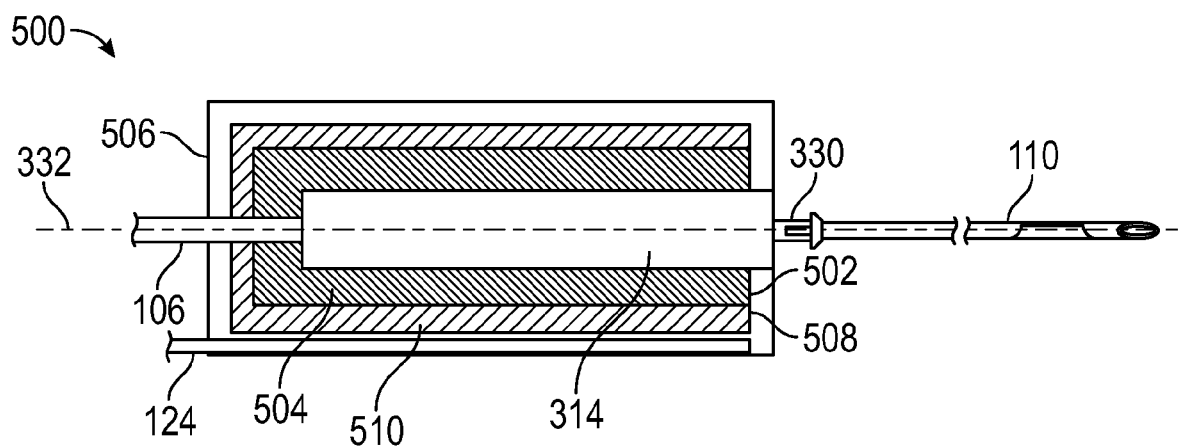
FIG. 5 shows a partial cross-section of a handset according to certain embodiments of the present disclosure

FIG. 5 shows a partial cross-section of a handset 506 comprising the fluid line 124 and a first container 502 comprising a first phase-change material 504. It is appreciated that a surgical handset such as the handset 506 comprises additional components not illustrated in FIG. 5, such as components employed for power, temperature and performance monitoring, fluid/suction, and other components that may be used for the operation of the surgical handset. The handset 506 is coupled to an instrument 110 at the distal end 324 of the handset 506 via the coupler 330. In this example, a second container 508 comprising a second phase-change material 510 is telescoped over the first container 502. The second container 508 may be telescoped over the first container 502 prior to activation of the handset 506, and in alternate embodiments, the second container 508 may be telescoped over the first container 502 when the handset 506 is deactivated and then reactivated after the second container 508 is telescoped. In an embodiment, the second phase-change material 510 may comprise a different phase-change temperature than the phase-change temperature associated with the first phase-change material 504, and may be in the same state or in a different (initial) state than the first phase-change material 504. In alternate embodiments additional containers (not shown) may be telescoped over the second container 508, these additional containers may comprise phase-change materials of varying types. In this example, a third or a fourth container may be telescoped as described above, these containers may contain phase-change material with a higher phase-change temperature than previously telescoped containers. Additional containers may be employed, for example, for longer procedures so that the procedure is not interrupted by the automatic deactivation of the handset. The phase-change temperature of the PCM in each container could be selected such that as the phase fully changes in the first container and the temperature rises slightly, the second container then starts absorbing heat radiated from the first container, yet still keeping the overall device below prescribed limits. In other cases, the phase change material may have the same phase-change temperature. In some embodiments, the use of additional containers may eliminate or reduce the likelihood of the automatic deactivation, and therefore save the time it would have taken during the procedure or change the container(s) or switch out the entire handset.

Figure 6A:
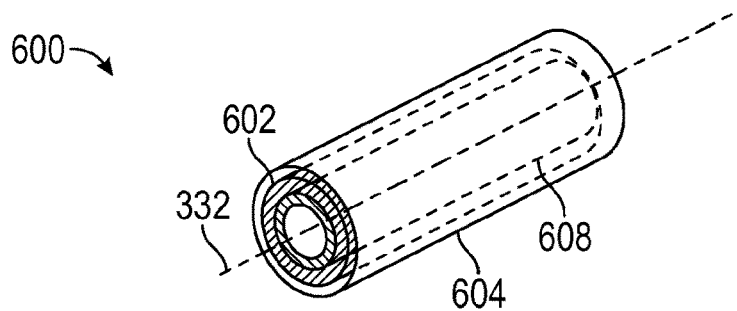
FIGS. 6A-6D shows a handset where a container filled with phase-change material is removed after use and replaced.
Figure 6B:
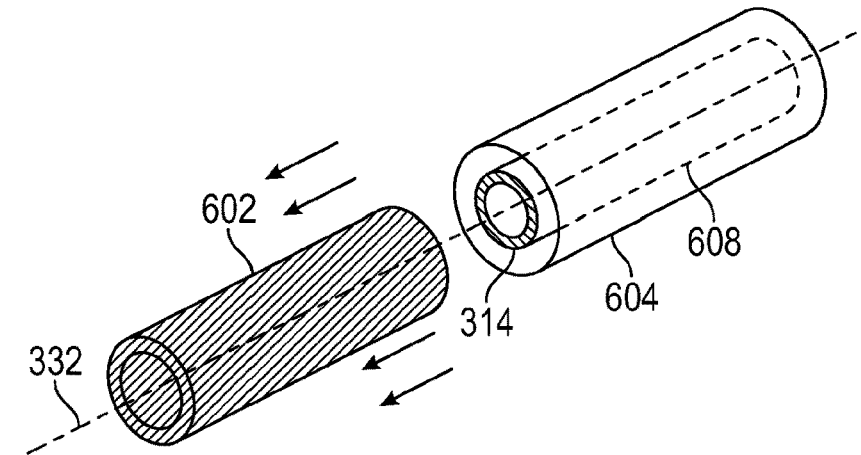
Figure 6C:
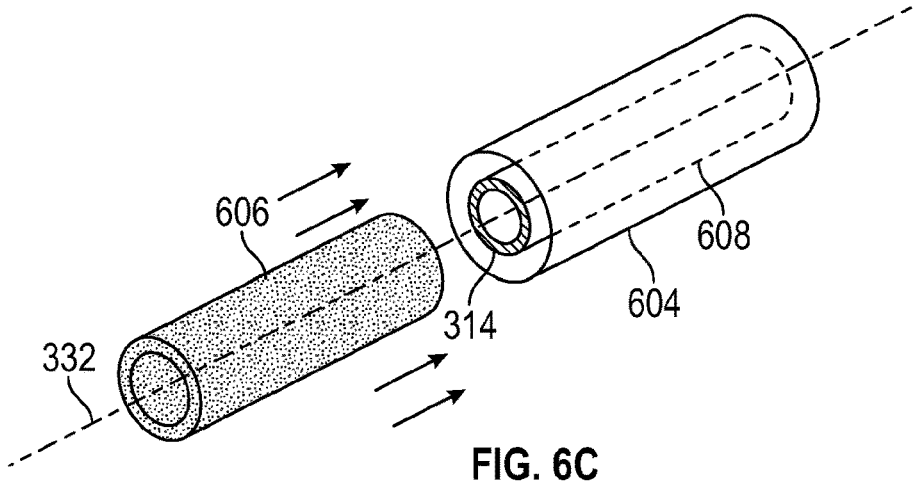
Figure 6D:
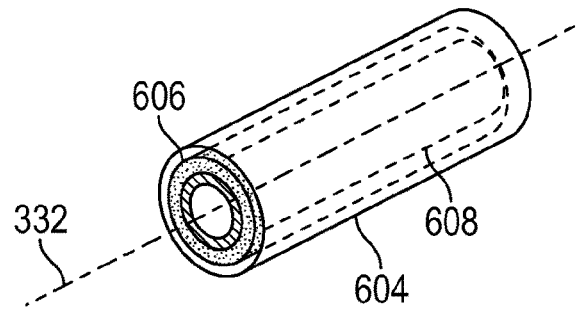

FIGS. 6A-6D are illustrations of a handset where a container filled with phase-change material is removed after use and replaced. It is appreciated that the handset 604 illustrated in FIGS. 6A-6D are partial illustrations, shown for the removal and replacement of the container 602 and therefore do not illustrate various fluid and power connections that may be present, nor the various internal components of the handset 604 that may couple to and/or enable the operation of the handsets. FIG. 6A illustrates the handset 604 comprising a first container 602 telescoped over a heat-generating mechanism 608 along a shared central axis 332. The heat-generating mechanism 608 may comprise a motor, a battery, or combinations thereof. FIG. 6B illustrates the removal of the container 602 from the heat-generating mechanism 608 to which it was at least one of thermally, mechanically, and electrically coupled. The removal depicted in FIG. 6B may be in response to the phase-change material of the container 602 fully transitioning from a first phase to a second phase, after which point the heat-absorbing properties of the container 602 may no longer be desirable and the instrument is automatically deactivated as discussed herein. The container 602 may then be replaced, as shown in FIG. 6C, or, as discussed in various embodiments, additional containers may be telescoped over the container 602 (not shown), and/or the container 602 may have the phase-change material removed and replaced. In FIG. 6C, a new container 606 is telescoped over the heat-generating mechanism 608 along the shared central axis 332, resulting in the embodiment in FIG. 6D of the re-assembled handset 604 comprising the new container 606. The new container 606 may comprise the same phase-change material as the container 602, or may comprise a different phase-change material with respect to the type of material and/or the phase-change temperature of the material.

Figure 7:
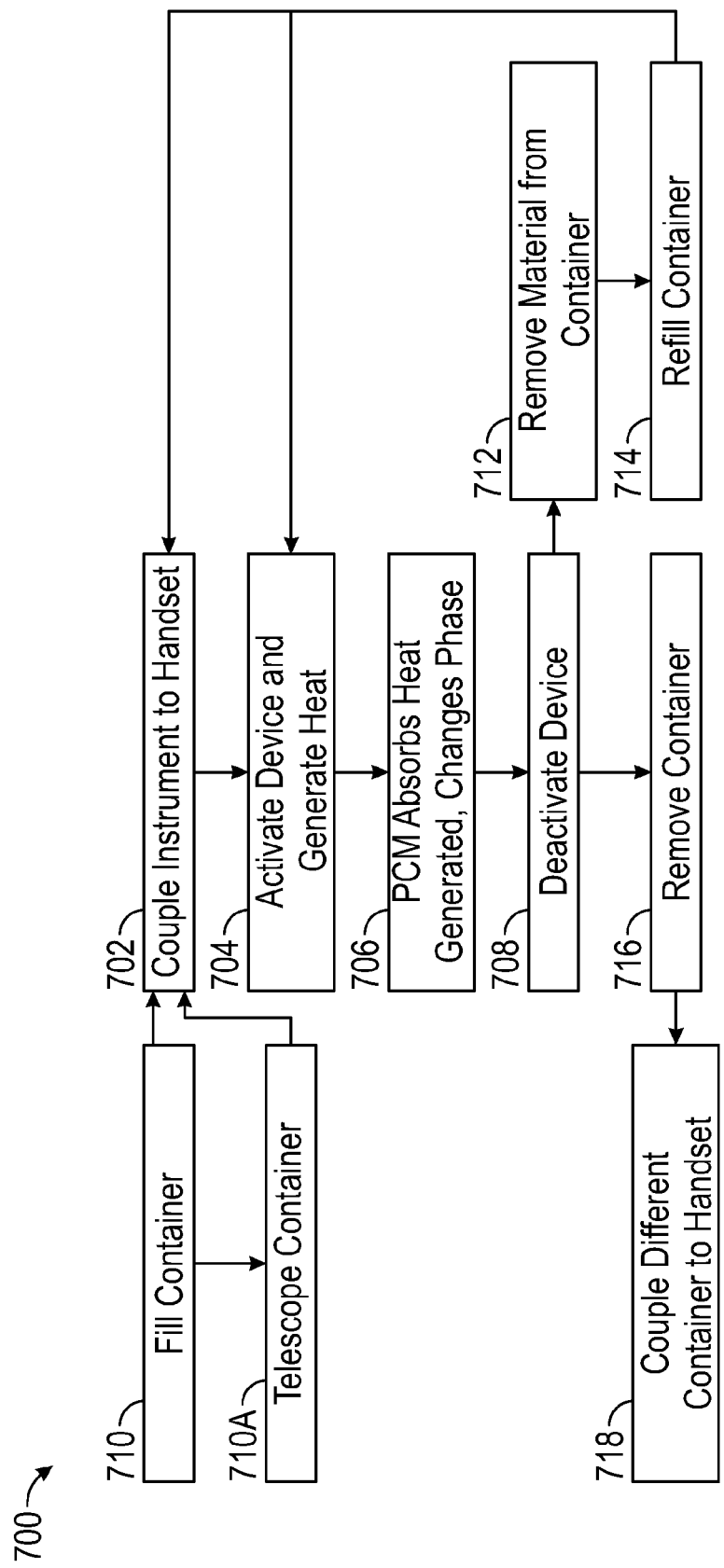
FIG. 7 shows a method of using a surgical device according to certain embodiments of the present disclosure.

FIG. 7 is a method 700 of using a surgical device. At block 702 of the method 700, a mechanical resection device (instrument) is coupled to a distal end of a handset. The handset may comprise a heat-generating mechanism such as a battery and/or a motor, as well as a container telescoped over the heat-generating mechanism. The container defines a first closed volume and is at least thermally coupled to the heat-generating mechanism. As discussed above, a phase-change material is disposed within the first closed volume, and the phase change material associated with a phase change temperature beyond which the material is associated with a second, different phase. In some examples, the first phase comprises a solid and the second a liquid, and in other examples the first phase may comprise a liquid and the second a gas. In an embodiment when the heat-generating mechanism is a motor, the method further comprises mechanically and thermally coupling the container to a stator of the motor. At block 704, the mechanical resection device is activated by a user and generates heat in response to the activation. At block 706, the phase-change material absorbs at least some of the heat generated which thereby causes the phase-change material, over time, to change phase from the first phase to a second phase. At block 708, in response to a determination by a circuit board of the handset that may be coupled to a temperature sensor of the handset that the temperature of the phase-change material is greater than the phase change temperature, the instrument is automatically deactivated.

In some embodiments, at block 710, either prior to or subsequent to telescoping the container over the heat-generating mechanism, the container is a refillable container that is filled with the phase-change material, and telescoped over the heat-generating mechanism at block 710A. In some embodiments, the handset may have had the container telescoped over the heat-generating mechanism prior to coupling the device to the handset at block 702, e.g., it may be presented to the surgeon as assembled, and in alternate embodiments, regardless of whether the container is filled immediately before or at an original equipment manufacturer (OEM), the container may be telescoped over the heat-generating mechanism at block 710A by the device operator prior to coupling the device to the instrument. In some embodiments, a single container may be telescoped over the heat-generating mechanism, and, in alternate embodiments multiple containers may be telescoped over each other, and may be removed, replaced, drained, and/or refilled as discussed herein with respect to the single-container embodiments. In this example, at block 712, the fully transitioned phase-change material of the container may be removed, and the container may be subsequently refilled at block 714. In some embodiments, the phase-change material may be removed/refilled at blocks 712 and 714 by way of ports in the handset that comprise valves, and the replacement phase-change material may be the same material, a similar material with a variation in composition, a different material with a similar phase-change temperature, or a different material with a different phase-change temperature. The container may be refilled without uncoupling it from the handset, in which instance the method would continue at block 704 where the handset comprising the refilled container would be reactivated. In an embodiment where the container is removed prior to one of removing or refilling the container with phase-change material, the method may start from block 702 where the refilled container may be recoupled to the handset. In an alternate embodiment, the method 700 further comprises removing the container from the handset at block 716 subsequent to deactivation at block 708, telescoping a different container over the handset at block 718 and coupling the different container to the handset, and re-activating the mechanical resection device at block 704.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A tissue removal system, comprising:
   a motor drive unit (MDU) that comprises a proximal end, a distal end, a motor, and a drive shaft, and an overall length;
   a mechanical resection device comprising a shaft, a resection tip at the distal end of the shaft, and a connector assembly on a proximal end of the shaft, the mechanical resection device removably coupled to the distal end of the MDU and rotationally coupled to the drive shaft by way of the connector assembly;
   a first container that defines a first closed volume, the first container thermally coupled to the MDU;
   a first phase-change material disposed within the first closed volume, the first phase change material thermally coupled to the MDU by way of the first container;
   a temperature sensor thermally coupled to the first container; and
   a control circuit associated with the MDU, the control circuit electrically coupled to the temperature sensor, wherein the control circuit is configured to read, from the temperature sensor, a value indicative of a temperature of the first phase-change material, and wherein the control circuit is further configured to deactivate the motor of the MDU when the value indicative of the temperature exceeds a predetermined threshold.

2. The system of claim 1, wherein the first container is removably coupled to the MDU.

3. The system of claim 1, wherein the first container is permanently affixed to the MDU.

4. The system of claim 1, further comprising:
   a second container that defines a second closed volume; and
   a second phase-change material disposed within the second closed volume,
   wherein the second container is thermally coupled to the first container.

5. The system of claim 1, wherein the first phase-change material is a solid at room temperature, and the first phase-change material configured to transition to a liquid upon absorption of heat.

6. The system of claim 1, wherein the first phase-change material is a liquid at room temperature, and the first phase-change material configured to transition to a gas upon absorption of heat.

7. The system of claim 1, further including a battery within the MDU, wherein the battery generates heat during use.

8. The system of claim 1, wherein the first container is mechanically and thermally coupled to a stator of the motor.

9. The system of claim 1, wherein the predetermined threshold is indicative of the first phase-change material fully transitioning from a first phase to a second phase.

10. The system of claim 1:
wherein the first container is metallic and the first container defines a first passage at least partially through the first container, the first passage fluidly isolated from the first closed volume;
wherein the motor comprises a stator; and
wherein the motor is telescoped within the first passage such that the stator of the motor is mechanically and thermally coupled to an inside surface of the first passage.

11. The system of claim 10, further comprising:
a second container that defines a second closed volume, the second container is metallic, and the second container defines a second passage at least partially through the second container, the second passage fluidly isolated from the second closed volume; and
a second phase change material disposed within the second closed volume,
wherein the first container is telescoped within the second passage such that the first container is mechanically and thermally coupled to an inside surface of the second passage.

* * * * *